United States Patent
Yoshida et al.

(10) Patent No.: US 6,649,179 B2
(45) Date of Patent: Nov. 18, 2003

(54) METHOD FOR IMPROVING MORBID DERMATITIS BY INHIBITING ACTIVITY OF A PLASMINOGEN ACTIVATOR IN THE SKIN

(75) Inventors: Yuzo Yoshida, Yokohama (JP); Eriko Kawai, Yokohama (JP)

(73) Assignee: Shiseido Co., Ltd., Tokyo (JP)

( * ) Notice: Subject to any disclaimer, the term of this patent is extended or adjusted under 35 U.S.C. 154(b) by 0 days.

(21) Appl. No.: 10/202,015

(22) Filed: Jul. 25, 2002

(65) Prior Publication Data

US 2003/0099721 A1 May 29, 2003

Related U.S. Application Data

(63) Continuation of application No. 09/741,039, filed on Dec. 21, 2000, now abandoned.

(30) Foreign Application Priority Data

Dec. 24, 1999 (JP) ............................................. 11-367773

(51) Int. Cl.$^7$ .......................... A61K 7/00; A61K 7/021; A61K 7/035
(52) U.S. Cl. ......................... 424/401; 424/400; 424/59; 424/78.03; 514/861; 514/859
(58) Field of Search .............................. 424/401, 400, 424/59, 78.03; 514/861, 859

(56) References Cited

U.S. PATENT DOCUMENTS 6,235,270 B1    5/2001    Ishii et al.

FOREIGN PATENT DOCUMENTS

| EP | 0 824 086 A | 2/1998 |
|---|---|---|
| FR | 2 729 132 A | 7/1996 |
| JP | 57062220 A2 | 4/1982 |
| JP | 60-33766 | 12/1982 |
| JP | 4-63046 | 12/1984 |
| JP | 6-76330 | 8/1985 |
| JP | 5-77644 | 2/1986 |
| JP | 1190625 A2 | 7/1989 |
| JP | 2628058 | 7/1989 |
| JP | 1308819 A2 | 12/1989 |
| JP | 2023361 A2 | 1/1990 |
| JP | 3169822 A2 | 7/1991 |
| JP | 3183620 A2 | 8/1991 |
| JP | 5117127 A2 | 5/1993 |
| JP | 06009363 A * | 1/1994 |
| JP | 6157277 A2 | 6/1994 |
| JP | 6239728 A2 | 8/1994 |
| JP | 7277914 A2 | 10/1995 |
| JP | 7304665 A2 | 11/1995 |
| JP | 8217616 A2 | 8/1996 |
| JP | 9-529975 | 8/1997 |
| JP | 10087434 A2 | 4/1998 |
| JP | 10087467 A2 | 4/1998 |
| JP | 10087468 A2 | 4/1998 |
| JP | 11193354 A2 | 7/1999 |
| WO | WO 94 07509 A | 4/1994 |

OTHER PUBLICATIONS

Database WPI, XP–002165439 & JP 09 143063 A (Itano Reito KK), Section Ch, Week 199732, Derwent Publication Ltd., London, GB, Jun. 3, 1997.
Database WPI, XP–002165440 & JP 03 017011 A (Toray Ind Inc.), Section Ch, Week 199110, Derwent Publication Ltd., London, GB, Jan. 25, 1991.
Database WPI, XP–002165441 & JP 06 219922 A (Kanebo Ltd.), Section Ch, Week 199436, Derwent Publication Ltd., London, GB, Aug. 9, 1994.
Database WPI, XP–002165442 & JP 07 277939 A, (Dowa Mining Co., Ltd.) Section Ch, Week 199551, Derwent Publication Ltd., London, GB, Oct. 24, 1995.
Database WPI, XP–002165443 & JP 11 193354 A (Fuji Shikiso KK), Section Ch, Week 199939, Derwent Publication Ltd., London, GB, Jul. 21, 1999.
Haustein, U.F., "Die Lokalisation des Gewebsaktivators der Fibrinolyse bei Dermatosen," *Arch. klin. exp. Derm.*, 1969, pp. 182–193, 234.
Fraki, Jorma, et al., "Human Skin Proteases," *Archives for Dermatological Research*, 1976, pp. 113–126, 256.
Lotti, T., et al., "Plasminogen Activators and Antiplasmin Activity in Atopic Dermatitis," *International Journal of Dermatology*, Sep. 1989, pp. 457–459, Vol 28, No. 7.
Kitamura, Kenji, et al., "Research on the Mechanism by which Dry Skin Occurs and the Development of an Effective Compound for its Treatment," *Japanese Society of Cosmetic Chemistry*, 1995, pp. 133–145, Vol 29, No. 2 (English Abstract, Figures, Bibliography).

* cited by examiner

Primary Examiner—Michael G. Hartley
Assistant Examiner—Mina Haghighatian
(74) Attorney, Agent, or Firm—Snider & Associates; Ronald R. Snider

(57) ABSTRACT

The present invention relates to a plasminogen activator inhibitor, an external preparation for skin comprising the same, a method for improving rough skin and in particular, for improvement of an effective inorganic component. A plasminogen activator inhibitor contains a specific zinc oxide which adsorbs a plasminogen activator and effectively inhibits its activity. When it is used as an external preparation for skin, excellent improvement of rough skin is obtainable. Further, when silica-coated zinc oxide is applied as an external preparation for skin, excellent improvement effect and prevention effect for rough skin are obtainable without an intolerance sensitivity reaction in the case of morbid dermatitis such as atopic dermatitis or pimpled skin.

12 Claims, No Drawings

METHOD FOR IMPROVING MORBID DERMATITIS BY INHIBITING ACTIVITY OF A PLASMINOGEN ACTIVATOR IN THE SKIN

RELATED APPLICATIONS

This application claims the priority of Japanese Patent Application No. 11-367773 filed on Dec. 24, 1999, which is incorporated herein by reference. This application is a continuation of application Ser. No. 09/741,039, filed on Dec. 21, 2000 now abandoned.

FIELD OF THE INVENTION

The present invention relates to a plasminogen activator inhibitor, an external preparation for skin comprising the same, a method for improving rough skin and in particular, to improvement of an effective inorganic component.

BACKGROUND OF THE INVENTION

It has been known that various kinds of medicines, external preparations for skin and cosmetics are effective for improvement and prevention of such symptoms as skin disease, rough skin and pimples. As an effective component of these medicines and cosmetics, for example, essences extracted from plants or animals which are effective for anti-inflammation, or those having moisture retaining or water retaining effect such as amino acids, polysaccharide, lipid and natural polymer have been used because these components are effective for prevention of dermatitis or prevention of water volatilization from a horny layer of epidermis.

On the other hand, especially careful selection of effective components should be needed in case of morbid dermatitis like atopic dermatitis or serious skin pimples because there is a possibility that said effective components cause intolerance sensitivity reaction or irritation in such cases.

Further in some cases those molecules such as organic polymers used as effective components for rough skin permeate into skin by a percutaneous absorption and have a probability to give other undesired skin effects. But if it is possible to use a solid powder that does not permeate into skin by a percutaneous absorption as an effective component for improvement of rough skin, an external preparation for rough skin comprising such a powder can be used more safely relative to previously used preparations containing organic molecules as the effective components.

However, the effect on improvement or prevention of the above-mentioned components provided previously was not sufficient. Further an effective medicine which is safe and free from irritation has been required because dermatitis, especially morbid dermatitis like atopic dermatitis, is accompanied by inflammation and a failure of a barrier function.

SUMMARY OF THE INVENTION

In view of the foregoing problems described above, an object of the present invention is to provide a plasminogen activator inhibitor which is effective for improvement of rough skin and an external preparation for skin comprising the same.

As a result of diligent studies for attaining the above mentioned object, we have found that a specified zinc oxide shows an activation inhibition effect on a plasminogen activator and also shows an improvement effect on rough skin when an external preparation for skin comprising said specified zinc oxide was used. And we have simultaneously found it is possible to use a powder as an effective component for improvement of rough skin.

A plasminogen activator inhibitor of the present invention comprises zinc oxide which adsorbs a plasminogen activator and inhibits its activity.

An adsorption rate of a plasminogen activator inhibitor of the present invention is preferably more than 60 percent per total amount, and an inhibition rate of a plasminogen activator inhibitor of the present invention is preferably more than 60 percent per total amount.

An adsorption rate and an inhibition rate are measured as follows:

Measurement of Adsorption Effect on a Plasminogen Activator

After mixing 0.1 percent of a tested sample and 1 μg/ml of a single chain-urokinase in a buffer solution for a fixed time, the sample was taken away from the buffer solution, and then an adsorption rate was determined by measuring the amount of a single chain-urokinase left in the buffer solution quantitatively by ELISA method.

Measurement of Activation Inhibition Effect on a Plasminogen Activator

An inhibition rate was determined by measuring a decomposition activity for a synthetic substrate caused by a buffer solution comprising 0.1 percent of a tested sample and 100 U/ml of a urokinase type plasminogen activator.

An adsorption rate of a plasminogen activator inhibitor of the present invention is especially preferable to be more than 70 percent per total amount, and an inhibition rate of a plasminogen activator inhibitor of the present invention is especially preferable to be more than 70 percent per total amount.

It is preferable to use zinc oxide coated by 0.1 to 70 percent by weight of silica at the present invention.

An external preparation for rough skin of the present invention is characterized by comprising powder which adsorbs a plasminogen activator and inhibits its activity.

An external preparation for rough skin of the present invention is characterized by comprising zinc oxide which adsorbs a plasminogen activator and inhibits its activity.

An external preparation for diseased skin of the present invention is characterized by comprising silica-coated zinc oxide which adsorbs a plasminogen activator and inhibits its activity.

A method for restraining activity of a plasminogen activator of the present invention is characterized by adsorbing a plasminogen activator on powder and inhibiting its activity.

A method to improve rough skin of the present invention is characterized by applying powder to skin which adsorbs a plasminogen activator and inhibits its activity.

An external preparation for rough skin of the present invention is characterized by comprising zinc oxide.

DETAILED DESCRIPTION OF THE INVENTION

The present invention of a plasminogen activator inhibitor and an external preparation for skin comprising it was accomplished based on the background described below.

It has been made clear recently that an activity change of a protease, especially an activity change of a fibrinogenolysis type enzyme (a plasminogen activating enzyme) such as plasmin or plasminogen activator, is closely related to a formation of various types of diseased skin accompanied with rough skin or abnormal cornification.

For example, it was reported that a distribution of plasmin in an epidermal cell layer of rough skin experimentally formed was changed relative to a distribution of plasmin in epidermal cell layer of normal skin, and anti-plasmin agent is effective for improvement and prevention of rough skin (Kenji Kitamura: J. Soc. Cosmet. Chem. Jpn; 29(2), 1995). Further in case of atopic dermatitis high fibrinogenolysis activity in epidermis was also reported (T. Lotti: Department of Dermatology; 28(7), 1989). On the other hand, in the case of psoriasis, representative of diseased skin accompanied with inflammation and abnormal cornification, it was reported that there exists high plasminogen activator activity at a portion of parakeratosis in an epidermis of the affected part (Haustein: Arch. Klin. Exp. Dermatol; 234, 1969), and it was also reported that a plasminogen activator was extracted from a flake of psoriasis by using a high-concentration buffer solution(Fraki, Hopsu: Arch. Dermatol. Res; 256, 1976).

A plasminogen activator is a protease which selectively acts on a plasminogen, (a precursor of plasmin) and transform plasminogen to active form.

Based on the above-mentioned existing background, the present inventors attempted to develop a new medicine for rough skin, and took notice of the fact that a plasminogen activator exists in a corneal layer of epidermis of rough skin like a flake of psoriasis. Then various kinds of inorganic powder were investigated for improvement and prevention of rough skin, based on the idea that a material which adsorbs and deactivates a plasminogen activator at a surface of skin and does not have the process of percutaneous absorption would be effective for improvement and prevention of diseased skin or rough skin which accompanies an activity change for a plasminogen activating enzyme, and also would be highly safe for human body. As a result of exploring various kinds of inorganic powder, it was found that a specified zinc oxide, especially silica-coated zinc oxide where a weight percent of coated silica is 0.1 to 70 weight percent per total weight, excellently adsorbs and inhibits a plasminogen activator. It was also found that an external preparation for skin comprising said specified zinc oxide excellently improves rough skin.

The embodiments of the invention will be disclosed below in greater detail.

In the present invention silica-coated zinc oxide where a weight percent of coated silica is 0.1 to 70 percent is preferably used as a specified zinc oxide which adsorbs a plasminogen activator and inhibits its activity. Silica which is described in the present specification is probable to be a form of hydrate, and it is also probable to be a form of non-hydrate.

Zinc oxide has been mainly used as an external preparation like cosmetics, or ultraviolet-scattering agent and as a white pigment. However its ultraviolet-scattering effect was not sufficient, and also there was a problem that the zinc oxide decreased stability of a formulation by its catalytic activity. Based on these problems, for the purpose of improvement of stability and utility of a formulation system without decreasing the ultraviolet-scattering function, zinc oxide which has more shorter particle diameter than that of previously used zinc oxide (Japanese Patent Publication No. Shou 60-33766, Japanese Patent Publication No. Hei 5-77644) or a complex with various inorganic or organic compounds have been developed (Japanese Patent Laid Open No. Hei 1-190625, Japanese Patent Laid Open No. Hei 3-183620, Japanese Patent Laid Open No. Hei 7-277914, Japanese Patent Laid Open No. Hei 10-87434, Japanese Patent Laid Open No. Hei 10-87467, Japanese Patent Laid Open No. Hei 10-87468).

On the other hand, zinc oxide is registered in Japanese pharmaceutical codex, and is known to combine with protein existing on skin to form film and as a result having a pharmacological effect such as astriction, improvement of inflammation and protecting. Based on these pharmacological effects, zinc oxide has been used as a form of a mixture of zinc oxide, lanolin and white ointment or as a powder preparation mixed with those such as talc or starch for applying to diseased skin, rough skin by diaper and so on. Moreover, to add medical effect of zinc oxide to other materials, zinc oxide was applied to skin as a form of mixture with other agents such as an anti-inflammating agent, antibacterial material (Japanese Patent Publication No. Hei 4-63046, Japanese Patent Publication No. Hei 6-76330, Japanese Patent Laid Open No. Hei 2-23361, Japanese Patent Laid Open No. Hei 6-157277, Japanese Patent Laid Open No. Hei 8-217616, Japanese Patent Laid Open No. Shou 57-62220), anti-oxidation agent (Japanese Patent Laid Open No. Hei 7-304665) and protease inhibitor (Japanese Patent Laid Open No. Hei 3-169822), or as a form of a complex.

However, a report or a description rarely exists concerning the character of zinc oxide suitable for medicine, such as particle diameter, limitation of manufacturing method. Such a description only exists in Japanese patent laid open No. Hei 6-239728 where it is described that ultra-micro particle zinc oxide is more effective on astringent than zinc oxide previously used, but a concrete example is not described in that literature.

Although it has also been known that zinc oxide adsorbs protein, a detailed description has not been reported concerning an adsorption effect of protein of various kinds of zinc oxide, and also concerning the adsorption effect of a plasminogen activator on zinc oxide and the inhibition effect of its activity. As to this point the present inventors tested trypsin as a reference which is classified into a serine protease as same as a plasminogen activator. As a result of the trypsin test, the present inventors have found that its activity was maintained as same as before adsorption though the trypsin was adsorbed on zinc oxide. So it should be obvious that it can not be said that zinc oxide usually inhibits enzyme activity.

An external preparation for skin of the present invention comprises zinc oxide which adsorbs a plasminogen activator and inhibits its activity. It is preferable to use silica-coated zinc oxide as an effective component.

Generally manufacturing methods of zinc oxide can be classified into two methods, the dry method and the wet method. Due to the dry method zinc oxide is manufactured by oxidation of zinc plate in a suitable furnace at highly heating condition, or handling zinc hydroxide or zinc nitrate at highly heating condition (Zinc oxide manufactured by the dry method will be described as the dry method type zinc oxide hereafter.). On the other hand, due to the wet method zinc oxide is manufactured by precipitating basic zinc carbonate from sodium-carbonate solution containing zinc sulfate or zinc chloride following cleaning, drying and highly heating (A zinc oxide manufactured by the wet method will be described as the wet method type zinc oxide hereafter.). The dry method type zinc oxide tends to have better quality than the wet method type zinc oxide.

Zinc oxide with shorter particle diameter can be classified into micro particle type (its specific surface area is at least 10 m²/g) and ultra-micro particle type (its particle diameter is less than 0.1 μm).

In the present invention zinc oxide with an average particle diameter of less than 0.2 μm which is classified into micro particle type or ultra-micro particle type is more preferably used than a normal zinc oxide because of its effective property. Although a fluorescent zinc oxide manufactured by calcinating of zinc oxide under reduction-atmosphere with hydrogen or carbon monoxide (disclosed in Japanese Patent Laid Open No. Hei 5-117127) was tested, it showed little adsorption of a plasminogen activator and little inhibition of its activity, and also did not show any improvement of skin.

As stated above zinc oxide shows excellent property as to adsorption of a plasminogen activator and inhibition of its activation, but its detailed mechanism is not still clear at present.

For the purpose of improvement of properties such as ultraviolet scattering effect, safety, stability and usability, a complex powder has been developed which has a particle component composed of zinc oxide and a material that coats zinc oxide or is coated by zinc oxide, such as inorganic or organic compounds such as carbonate, sulfate (Japanese Patent Laid Open No. Hei 10-87468), meta-magnesium silicate aluminate (Japanese Patent Laid Open No. Hei 1-308819), silica, alumina (Japanese Patent Laid Open No. Hei 3-183620, Japanese Patent Laid Open No. Hei 10-87467), organofluorinated modified silicone (Japanese Patent Laid Open No. Hei 7-277914), polyester, nylon and cellulose (Japanese Patent No. 2628058).

When zinc oxide is coated by silica, adsorption of a plasminogen activator and inhibition of its activity is improved more than when a normal zinc oxide is used. Moreover irritation is moderated when applied to a sensitive skin damaged by inflammation when silica-coated zinc oxide was used. So silica-coated zinc oxide is more preferably used for the present invention than a normal zinc oxide. Although the manufacturing method and particle size of zinc oxide used as a carrier of a plasminogen activator of the present invention is not limited, zinc oxide which non-fluorescent and an average particle diameter of less than 0.2 μm is preferably used for the reason that it has more effective adsorption of a plasminogen activator and inhibition of plasminogen activity, and more effective improvement of skin results.

Zinc oxide coated by 0.1 to 70 weight percent of silica, more preferably coated by 5 to 40 weight percent of silica, is preferably used. No effect is evident when zinc oxide coated by less than 0.1 weight percent of silica is used. The effect of the present invention is lowered when zinc oxide coated by more than 70 weight percent of silica is used.

Although some types of silica-coated zinc oxide have been known with different manufacturing methods or a different construction of coating layers (Japanese Patent Laid Open No. Hei 3-183620, Japanese Patent Application No. Hei 9-529975, Japanese Patent Laid Open No. Hei 10-87434, Japanese Patent Laid Open No. Hei 11-193354), any zinc oxide can be used for the present invention with a limitation of weight percentage of silica mentioned above.

When zinc oxide of the present invention is used as an external preparation for skin, it can be treated with materials like silicone for giving hydrophobic property on its surface if needed.

An external preparation for skin of the present invention can comprise one or more types of zinc oxides mentioned above and gives excellent effect on adsorption of plasminogen activator and inhibition of its activity, improvement of skin results, and it is very safe.

Two kinds of plasminogen activator are known. One is called urokinase and exists in healthy epidermis and the other is called organized plasminogen activator and exists in morbid skin.

Zinc oxide of the present invention has an effect for both types of plasminogen activator mentioned above. The effect is on adsorption of plasminogen activator and on inhibition of plasminogen activity.

A sensitive symptom or irritation appears occasionally when a patient suffering from atopic dermatitis or serious pimpled skin uses an external preparation for skin containing a high concentration zinc oxide. However such symptoms do not appear when the silica-coated zinc oxide of the present invention is used. Therefore silica-coated zinc oxide of the present invention is especially effective for an external preparation for skin used to improve serious dermatitis.

The preferable combination amount of zinc oxide in an external preparation for skin of the present invention is 0.005 to 50.0 weight percent per total amount, more preferably 0.1 to 20.0 weight percent per total amount. When used with less than 0.005 weight percent the effect of the present invention is not sufficient, and when used with more than 50.0% weight percent it is difficult to formulate an external preparation for skin.

If the effect of the present invention is maintained, an external preparation for skin of the present invention can include components usually applicable to an external preparation for skin used as cosmetics or medicines, such as moisture retaining agents, oil ingredients, ultraviolet absorbent, emulsifiers, surfactants, thickeners, alcohols, powder components, colorants, hydrophilic components, water, skin eutrophic medicine.

Further an external preparation for skin of the present invention can comprise: a sequestering agent such as disodium EDTA, trisodium EDTA, sodium citrate, sodium polyphosphate, sodium metaphosphate, gluconic acid and malic acid: plant extracts such as glycyrrhiza extract, Chinese quince extract, ichiyakusou extract: medical components such as caffeine, tannin, verapamil, tranexamic acid and its derivatives, tocopherol acetate, glycyrrhezinic acid and its derivatives or salts,: whitening agents such as vitaminC, magnesium ascorbate phosphate, glucoside ascorbate, arbutin, kojic acid,: amino acids and its derivatives such as arginine, lysine,: saccharides such as fructose, mannose, erythritol, trehalose, xylitol: and so on.

An external preparation for skin of the present invention can be applied in a form such as ointment, cream, lotion, pack, foundation, lipstick, bath composition, paper for oil absorption, paper powder and other forms normally used for external for skin preparations. A shape of said external preparation for skin is arbitrary.

In the following, the present invention will be explained by using specific examples. However, the present invention should not be restricted thereto. Unless otherwise stated, quantities are expressed as weight percent.

Before disclosure of examples, the test procedures and the results concerning adsorption effect of zinc oxide of the present invention for a plasminogen activator, activation inhibition effect of zinc oxide of the present invention for a plasminogen activator and improvement effect of skin caused by zinc oxide of the present invention are explained.

1. Test Procedure for Examining the Adsorption Effect and Inhibition Effect of Zinc Oxide of the Present Invention for a Plasminogen Activator (in vitro)

1-1 Sample Preparation

An inorganic powder such as talc, mica, kaolin, zeolite, sericite, sodium magnesium metasilicate, hydroxyapatite, aluminium oxide, silica, titanium oxide, and eight kinds of zinc oxides with different properties such as particle diameter or manufacturing method((1)~(8)) were used as samples. 0.1 percent of a sample was suspended in water and the adsorption/activation inhibition effect was evaluated.

1-2 Measurement of Adsorption Effect of Zinc Oxide of the Present Invention for a Plasminogen Activator Tris-HCl buffer(pH 7.4) was added into 20 $\mu$l of a sample suspension to give total amount of 180 $\mu$l, followed addition of 20 $\mu$l of a precursor type urokinase containing solution(10 $\mu$g/ml). The solution was left for five minutes at room temperature, and the sample powder was filtered and the filtrate was collected. The sample powder was washed sufficiently with a constant amount of Tris-HCl buffer, and the Tris-HCl buffer used for washing was added to the filtrate, and this solution was used as the non-adsorbent urokinase containing solution. The concentration of said non-adsorbent urokinase containing solution was determined by the ELISA method using TintElize uPA(biopool), and then the amount of the urokinase adsorbed on the sample powder was caluculated. The results are shown in Table 1.

1-3 Measurement of Activation Inhibition Effect of Zinc Oxide of the Present Invention for a Plasminogen Activator Tris-HCl buffer(pH 7.4) was added in 20 $\mu$l of a sample suspension to give the total amount of 180 $\mu$l, following addition of 20 $\mu$l of an activator type urokinase containing solution (1000 U/ml). The solution was left for fifteen minutes in a thermostatic chamber at 37° C., and 20 $\mu$l of S2444 (CHROMOGENIX), specified synthetic substrate of urokinase, was added to the solution, and the solution was left for fifteen minutes at 37° C. Then the reaction was stopped by adding 20 $\mu$l of water solution containing 12 percent of trichloroacetic acid, then the sample powder was filtered and activity of urokinase was derived by measuring absorbance of the filtrate at 405 nm, then activation inhibition rate of a plasminogen activator was calculated. The results are shown in Table 1.

2. Test for Evaluating the Rough Skin Prevention Effect Caused by Zinc Oxide of the Present Invention (in vivo)

2-1 Sample Preparation

As same as the test procedure at the condition in vitro, talc, mica, kaolin, zeolite, sericite, sodium magnesium matasilicate, hydroxyapatite, aluminium oxide, silica, titanium oxide and eight kinds of zinc oxides with different particle diameters or manufacturing methods, eighteen samples by total, were selected as samples and a sample suspension was prepared by suspending 3 percent of a sample powder in water. Then the rough skin prevention effect caused by zinc oxide of the present invention was evaluated.

2-2 Judgment of the Rough Skin Prevention Effect Caused by Zinc Oxide of the Present Invention A cotton sheet(2×2 cm) soaked by 5 percent of SDS solution was put on inside of each forearm of panelists composed of 54 men and left alone for fifteen minutes. The surfactant stuck on a forearm of a panelist was washed out, and then 0.5 ml of a sample suspension selected for each panelist was applied on the portion where said cotton sheet was put, and 0.5 ml of water was also applied as a reference on the portion where said cotton sheet was put and the sample suspension was not applied (n=3). This procedure, applying the sample and water, was daily repeated for seven days. After seven days past, the tested portion was sufficiently washed, and left for 60 minutes, then a condition of rough skin caused by SDS was observed and the evaluation point was decided based on the judgment standard described below. The difference of the evaluation point between the sample applied portion the reference portion was derived for each panelist, and the differences derived were summed for each sample, and the rough skin prevention effect of each sample was judged based on the judgment standard described below. The results are shown in Table 1 with the results in vitro.

The Standard Used to Decide the Evaluation Point Concerning the Condition of Rough Skin The evaluation point 4: An obvious erythema and/or scaled horny layer was observed.
The evaluation point 3: A medium erythema and/or a little degree of scaled horny layer was observed.
The evaluation point 2: A little erythema and/or a crack in horny layer was observed.
The evaluation point 1: The surface of horny layer looks white, or looks like powder-attached.
The evaluation point 0: No symptom was observed.

The Judgment Standard for the Rough Skin Prevention Effect

TABLE 1

| Sample (character) | Adsorption rate % | Inhibition rate % | Rough skin prevention effect |
|---|---|---|---|
| Talc | 68.1 | 3.9 | X |
| Mica | 60.3 | 11.5 | X |
| Kaolin | 70.1 | 0 | X |
| Zeolite | 28.0 | 0 | X |
| Sericite | 68.5 | 0 | X |
| Sodium magnesium metasilicate | 84.2 | 0 | X |
| Hydroxyapatite | 0 | 0 | X |
| Aluminium oxide | 11.0 | 0 | X |
| Silica | 70.1 | 0 | X |
| Titanium oxide | 39.1 | 0 | X |
| Zinc oxide (1) (average diameter 0.5 $\mu$m, the dry method type) | 47.9 | 54.1 | Δ |
| Zinc oxide (2) (average diameter 0.4 $\mu$m, the wet method type) | 38.5 | 56.0 | Δ |
| Zinc oxide (3) (average diameter 0.04 $\mu$m, the wet method type) | 30.1 | 56.4 | Δ |
| Zinc oxide (4) ((1) was calcinated under hydrogen atmosphere = a fluorescent zinc oxide) | 15.6 | 52.2 | X |
| <Zinc oxides of the present invention> | | | |
| Zinc oxide (5) (average particle diameter 0.02 $\mu$m, the wet method type) | 69.7 | 63.6 | ◯ |
| Silica-coated zinc oxide (6) ((1) was coated by 30% of silica.) | 76.9 | 72.1 | ◉ |
| Silica-coated zinc oxide (7) ((2) was coated by 30% of silica.) | 70.0 | 68.6 | ◯ |
| Silica-coated zinc oxide (8) ((5) was coated by 30% of silica.) | 84.5 | 77.8 | ◉ |

◉ = Obvious effect was recognized: more than 6 of the difference from the evaluation point
◯ = A little effect was recognized: 4 or 5 of the difference from the evaluation point
Δ = A trend of prevention was recognized: 2 or 3 of the difference from the evaluation point
X = No effect was recognized: less than 1 of the difference from the evaluation point It is recognized from the result in Table 1 that although most of the inorganic powder evaluated showed an adsorption effect of a plasminogen activator(urokinase), only zinc oxides showed an activation inhibition effect. On the other hand, although all zinc oxides showed a relatively high activation inhibition effect, the adsorption effect of a fluorescent zinc oxide (case(4)) was extremely low. When limited to the case of zinc oxides, the improvement effect on rough skin was proportional to adsorption effect on a plasminogen activator. From this tendency, it is understood that both adsorption effect and activation inhibition effect on a plasminogen activator are important for effectiveness on skin. And it is also understood that a sample powder, where both an adsorption rate and an inhibition rate are more than 60 percent, highly shows the rough skin prevention effect. Especially a sample powder where both an adsorption rate and an inhibition rate are more than 70 percent shows especially high rough skin prevention effect. Further it was understood that the adsorption effect and activation inhibition effect of zinc oxide for a plasminogen activator, and the rough skin prevention effect caused by zinc oxide were promoted by coating silica on a surface of zinc oxide.

The compared results for the cases where zinc oxide of (5) in Table 1, silica-coated zinc oxide of (8) in Table 1, a mixture of zinc oxide of (5) in Table 1 and silica are used are shown in Table 2.

TABLE 2

| Sample (character) | Adsorption rate % | Inhibition rate % | Rough skin prevention effect |
|---|---|---|---|
| Zinc oxide (5) (average diameter 0.02 μm, the wet method type) | 69.7 | 63.6 | ○ |
| Zinc oxide (5)/Silica mixture (the rate of weight = 7:3) | 82.1 | 68.8 | ○ |
| Silica-coated zinc oxide (9) ((5) was coated by 10% of silica.) | 79.0 | 69.0 | ○ |
| Silica-coated zinc oxide treated with silicone (10) ((8) was treated with 3% of silicone) | N.D. | N.D. | ○ |
| Silica-coated zinc oxide (8) ((5) was coated by 30% of silica.) | 84.5 | 77.8 | ⊙ |

It is recognized from the result in Table 2 that when a mixture of zinc oxide and silica is used, while the adsorption rate was improved, the inhibition rate is not remarkably improved. On the other hand, when silica-coated zinc oxide was used, the inhibition rate is remarkably improved. So it is reasonably understood that the rough skin prevention effect is extremely high in case where silica-coated zinc oxide was used.

Further in case where silica-coated zinc oxide with a coating weight less than 10 weight percent was used (case (9)), though the effect was a little inferior to the case of coating weight of 30 weight percent (case (8)), sufficient effect was recognized. Silica-coated zinc oxide not only had the effect of increasing improvement effect on rough skin, but also had the effect of softening irritation for a sensitive skin with serious dermatitis as described below, and these effects were observed in case where silica coating weight ranged from 0.1 to 70 weight percent, and were especially effective at the range 5 to 40 weight percent.

On the other hand, when silica-coated zinc oxide with a remarkable effect (case (8)) was treated with 3 percent of silicone to give a hydrophobic property (case (10)), the adsorption effect and inhibition effect could not be measured (N.D. in Table2) because said silica-coated zinc oxide did not disperse in the evaluation system for its hydrophobic property. But sufficient prevention effect of rough skin was observed when actually applied to skin, though the effect was inferior to untreated silica-coated zinc oxide (case (8)).

3. Test of Skin Improvement in Case of Actual Application 3-1 Test of Effectiveness on Atopic Dermatitis The effectiveness on improvement of atopic dermatitis was evaluated by applying a lotion of the present invention shown in Table 3 comprising silica-coated zinc oxide of a dry type with its particle diameter of 0.04 μm (FINEX-25 manufactured by SAKAI CHEMICAL Co. Ltd with silica coating weight of 20 percent) as a sample. And as a reference the dry method zinc oxide with its average particle diameter of 0.5 μm (manufactured by SAKAI CHEMICAL Co. Ltd, zinc oxide registered in Japanese pharmaceutical codex) was used (reference 1), and a lotion which do not comprise any zinc oxide was also used (reference 2).

The test procedure was as follows: 40 Patients who suffered from a light or medium symptoms of atopic dermatitis were divided into two groups consisting of 20 patients. Two portions with typical and same degree of eczema existing in both right and left side of contrasting position of the body were determined to be the tested portions. For the patients in one group the lotion of the present invention and the lotion of reference 2 were applied to each tested portion where it was arbitrary decided to which portion (right or left side) which lotion (the lotion of the present invention or the lotion of reference 2) was applied. For the patients in other group the lotion of reference 1 and the lotion of reference 2 were applied to each tested portion as same as the above-mentioned method. This procedure was daily repeated two times at morning and night time for 4 weeks. After 4 weeks passed, a condition of a erubescence and a dryness (scaled horny layer) in the tested portion was observed and a question was put to the patients about their itchy feeling, and based on the observation and the question the evaluation point was determined by the standard described below. The differences of the evaluation point between when the lotion of reference 2 was applied and the case where the lotion of the present invention was used, and also the difference of the evaluation point between when the lotion reference 2 was used and when reference 1 was used were derived and the improvement effect was judged based on the judgment standard described below. The results are shown in Table 4.

The Evaluation Point Standard

The evaluation point 4: a serious symptom
The evaluation point 3: a medium symptom
The evaluation point 2: a light symptom
The evaluation point 1: a very light symptom
The evaluation point 0: no symptom The Standard for Judgment of Improvement Effect Pronounced improvement: more than 3 of the difference from the evaluation point
Medium improvement: 2 of the difference from the evaluation point
A little improvement: 1 of the difference from the evaluation point
No improvement: 0 of the difference from the evaluation point
Worse symptom: less than −1 from the difference of the evaluation point

TABLE 3

| Sample (weight percent) | The lotion of the present invention | The lotion of reference 1 | The lotion of reference 2 |
|---|---|---|---|
| Zinc oxide (silica-coated FINEX-25) | 5.0 | — | — |
| Zinc oxide (registered in Japanese pharmaceutical codex) | — | 5.0 | — |
| Polyethylene glycol 400 | 12.0 | 12.0 | 12.0 |
| Grycerin | 7.0 | 7.0 | 7.0 |
| Polyoxyethylene (60) hydrogenated-castor oil | 1.0 | 1.0 | 1.0 |
| Ethyl alcohol | 40.0 | 40.0 | 40.0 |
| Pure water | rest | rest | rest |
| Perfume | suitable amount | suitable amount | suitable amount |

TABLE 4

| | a number of the case of pronounced improvement or medium improvement | a number of the case of a little improvement | a number of the case of no improvement | a number of the case of worse symptom |
|---|---|---|---|---|
| <Erubescence> | | | | |
| The lotion of the present invention | 5 | 11 | 4 | 0 |
| The lotion of reference 1 | 2 | 8 | 9 | 1 |
| <A dryness> | | | | |
| The lotion of the present invention | 8 | 9 | 3 | 0 |
| The lotion of reference 1 | 3 | 6 | 9 | 2 |
| <Itchy feeling> | | | | |
| The lotion of the present invention | 2 | 8 | 10 | 0 |
| The lotion of reference 1 | 1 | 7 | 12 | 0 |

It is obvious from the results of Table 4 that a much superior improvement effect was recognized for the lotion of the present invention than the reference lotion comprising other zinc oxides generally used as medicine. When the lotion of the present invention was applied no worse symptom was present while when the lotion comprising a zinc oxide generally used (reference 1) was applied a few cases of worse symptoms were recognized. A case of irritation caused by a zinc oxide was also recognized when the lotion comprising a zinc oxide generally used (reference 1) was applied. Silica-coated zinc oxide showed excellent property for applying as an external preparation for serious dermatitis.

3-2 Test of Effectiveness for Pimpled Skin

A foundation of the present invention is shown in Table 5 which comprises silica-coated zinc oxide of the wet method type with its average particle diameter of 0.03 $\mu$m (ACTIVOX manufactured by HARCROS with 20 percent of coating silica) was prepared as a sample. And a foundation containing the wet method type zinc oxide with its particle diameter of 0.04 $\mu$m (AZO-BS manufactured by SEIDO CHEMICAL Co. Ltd) was prepared as a reference (reference 3). Then the improvement effect on a pimpled skin was evaluated.

The test procedure was as follows: 40 Panelists of 16 to 24 year old women were divided to two groups each consisting of 20 panelists. A portion of the pimples in the face was decided to be a test portion. The foundation of the present invention was applied to the test portion of each panelist in one group, and the foundation of reference was applied to a test portion of each panelist in the other group. This application of the foundations was daily repeated for 4 weeks. After 4 weeks passed improvement of a pimples at a tested portion relative to the condition before beginning to test was evaluated by panelists themselves. Panelists were instructed to report their evaluation as a form of {A} or {B}, where {A} was selected in case where the symptom was improved and {B} was selected in case where the symptom was unchanged or worsened. And improvement effect was judged based on the standard described below. The results are shown in Table 5.

The Judgment Standard of Improvement Effect

TABLE 5

| Sample (character) | The foundation of the present invention | The foundation of reference 3 |
|---|---|---|
| Zinc oxide (silica-coated ACTIVOX) | 15.0 | — |
| Zinc oxide (silica-coated AZO-BS) | — | 15.0 |
| Sericite | 48.0 | 48.0 |
| Talc | 20.0 | 20.0 |
| Titanium dioxide | 6.5 | 6.5 |
| Iron oxide | 3.5 | 3.5 |
| Squalane | 6.0 | 6.0 |
| Sorbitan sesquioleate | 1.0 | 1.0 |
| <The improvement effect> | ◎ | Δ |

◎ = High improvement effect was recognized.: More than 15 panelists in 20 panelists evaluated to be {A}.
○ = An improvement was recognized.: 10 to 14 panelists in 20 panelists evaluated to be {A}.
Δ = A trend of improvement was recognized: 5 to 9 panelists in 20 panelists evaluated to be {A}.
X = An improvement was not recognized.: Less than 4 panelists in 20 panelists evaluated to be {A}.

It is recognized from the results in Table 5 that the improvement effect for pimpled skin when the foundation of the present invention was applied was much superior to that when the foundation of reference 3 was applied.

More specific examples of an external preparation for skin of the present invention will be described below.

EXAMPLE 1

Cream

| (Recipe) | Weight % |
|---|---|
| 1) Glyceryl monostearate | 2.0 |
| 2) Stearyl alcohol | 4.0 |
| 3) Beeswax | 3.0 |
| 4) Lanolin | 5.0 |
| 5) Ethyl paraben | 0.3 |
| 6) POE (20) sorbitan monoleate | 2.0 |
| 7) Squalane | 20.0 |
| 8) Zinc oxide (silica-coated FINEX-25) | 5.0 |
| 9) Perfume | 0.2 |
| 10) 1,3-Butylene glycol | 5.0 |
| 11) Glycerin | 5.0 |
| 12) Purified water | Balance |

Preparation Method

An oil phase was prepared by mixing all 1) to 7) and 9) with heating at 75° C. A water dissoluble phase was prepared by dissolving 10) and 11) into 12), and dispersing 8) into 12) with heating at 75° C. The water dissoluble phase was added to the oil phase and emulsified homogeneously by a homomixer. Then the mixture was cooled to 30° C. with mixing.

EXAMPLE 2

External Preparation with Powder Form

| (Recipe) | Weight % |
| --- | --- |
| 1) Talc | 49.95 |
| 2) Zinc oxide (silica-coated FINEX-50) | 50.0 |
| 3) Perfume | 0.05 |

Preparation Method 1) and 2) were mixed with a sufficient stirring by a blender and then 3) was spread homogeneously.

EXAMPLE 3

Baby Powder

| (Recipe) | Weight % |
| --- | --- |
| 1) Talc | 77.0 |
| 2) Calcium carbonate | 17.0 |
| 3) Starch | 0.5 |
| 4) Zinc oxide (silica-coated FINEX-75) | 5.0 |
| 5) Microbicide | 0.3 |
| 6) Antiseptic | 0.2 |

Preparation Method

All 1) to 6) were mixed with a sufficient stirring by a blender.

EXAMPLE 4

Lipstick

| (Recipe) | Weight % |
| --- | --- |
| 1) Hydrocarbon wax | 3.0 |
| 2) Candelilla wax | 1.0 |
| 3) Glyceryl isostearate | 40.0 |
| 4) Liquid paraffin | 46.448 |
| 5) Red No. 202 | 0.5 |
| 6) Red No. 204 | 2.0 |
| 7) Red No. 223 | 0.05 |
| 8) Zinc oxide (silica-coated ACTIVOX) | 3.0 |
| 9) Titanium dioxide | 4.0 |
| 10) Perfume | 0.002 |

Preparation Method

All 1) to 4) were dissolved with heating at 85° C. Then all 5) to 9) were added to the dissolved solution with mixing by a blender and 10) was added with mixing by a blender and then the mixture was filled up in a container and cooled.

EXAMPLE 5

Emulsified Foundation

| (Recipe) | Weight % |
| --- | --- |
| 1) Stearic acid | 0.4 |
| 2) Isostearic acid | 0.3 |
| 3) Cetyl-2-ethyl hexanoate | 4.0 |
| 4) Liquid paraffin | 11.0 |
| 5) POE (10) stearyl ether | 2.0 |
| 6) Talc | 15.0 |
| 7) Red iron oxide | 0.01 |
| 8) Yellow iron oxide | 0.001 |
| 9) Black iron oxide | 0.05 |
| 10) Cetyl alcohol | 0.3 |
| 11) Antiseptic | 0.07 |
| 12) zinc oxide (silica-coated FINEX-25 with silicone treated) | 5.0 |
| 13) Triethanol amine | 0.4 |
| 14) Propylene glycol | 5.0 |
| 15) Perfume | 0.01 |
| 16) Purified water | Balance |

Preparation Method

All 1) to 11) were dissolved with heating at 85° C., and then 12) was added into the mixed solution and dispersed to give an uniform mixture. 13), 14) and 16) were mixed with heating at 85° C. and this mixture was gradually added into said mixture of all 1) to 11) and emulsified. After stirring for 10 minutes at the temperature of emulsifying, the mixture was cooled with stirring to 45° C. 15) was added into this mixture with cooling to 35° C., and then the mixture was filled up in a container and cooled.

EXAMPLE 6

Pack

| (Recipe) | Weight % |
| --- | --- |
| 1) Polyvinyl alcohol | 15.0 |
| 2) Polyethylene glycol | 3.0 |
| 3) Propylene glycol | 7.0 |
| 4) Ethanol | 10.0 |
| 5) Zinc oxide(Silica-coated zinc oxide manufactured by SEIDO CHEMICAL Co. ltd) | 10.0 |
| 6) Methyl paraben | 0.05 |
| 7) Perfume | 0.1 |
| 8) Purified water | Balance |

Preparation Method

2), 3) and 6) were dissolved into 8). Then 1) was added and dissolved with heating, and 5) was dispersed in the mixture. 4) and 7) was added into the mixture and dissolved by stirring.

EXAMPLE 7

Stick Foundation

| (Recipe) | Weight % |
| --- | --- |
| 1) Titanium dioxide | 13.0 |
| 2) Kaolin | 12.0 |

-continued

| (Recipe) | Weight % |
|---|---|
| 3) Zinc oxide (silica-coated ACTIVOX) | 13.7 |
| 4) Red iron oxide | 1.0 |
| 5) Yellow iron oxide | 0.7 |
| 6) Black iron oxide | 0.1 |
| 7) Squalane | 37.0 |
| 8) Cetyl-2-ethyl hexanoate | 16.0 |
| 9) Sorbitan sesquioleate | 1.0 |
| 10) Microcrystalline wax | 4.0 |
| 11) Carnauba wax | 1.3 |
| 12) Perfume | 0.2 |

Preparation Method

All 7) to 9) were mixed at 80° C. and all 1) to 6) were added in the mixture and dispersed. Then TK mill treatment was done. 10) and 11) were added in the mixture and mixed, and then air was removed. 12) was gradually mixed in the mixture and then the mixture was filled up in a container and cooled.

EXAMPLE 8

Solid Powder Foundation

| (Recipe) | Weight % |
|---|---|
| 1) Sericite | 22.0 |
| 2) Synthetic mica | 15.0 |
| 3) Talc | Balance |
| 4) Silicic anhydride-coated zinc oxide (20 weight % of silicic anhydride, 0.03 μm of average particle diameter of zinc oxide) | 7.0 |
| 5) Red iron oxide | 0.8 |
| 6) Yellow iron oxide | 2.0 |
| 7) Black iron oxide | 0.1 |
| 8) Zinc white | 2.0 |
| 9) Elastic silicone powder | 2.0 |
| 10) Spherical polyethylene powder | 4.0 |
| 11) Dimethylpolysiloxane | 3.0 |
| 12) Fluid paraffin | 5.0 |
| 13) Vaseline | 5.0 |
| 14) Sorbitan sesquiisostearate | 1.0 |
| 15) Paraben | suitable amount |
| 16) Anti-oxidative agent | suitable amount |
| 17) Perfume | suitable amount |

Preparation Method

All 1) to 17) was sufficiently mixed by a blender.

EXAMPLE 9

W/O Type Emulsified Cosmetic Base

| (Recipe) | Weight % |
|---|---|
| 1) Cyclomethycone | 30.0 |
| 2) Dimethycone | 2.0 |
| 3) Silicone resin | 1.0 |
| 4) Anti-oxidative agent | suitable amount |
| 5) Octyl methoxycinnamate | 3.0 |
| 6) 4-tert-butyl-4'-methoxy benzoyl methane | 1.0 |
| 7) Isosterate | 1.0 |
| 8) Silica-treated alumina | 8.0 |
| 9) Cation-modified bentonite | 2.0 |

-continued

| (Recipe) | Weight % |
|---|---|
| 10) Composite material between zinc oxide and silicic anhydride (30 weight % of silicic anhydride, 0.1 μm of average particle diameter of zinc oxide) | 5.0 |
| 11) Talc | 5.0 |
| 12) Spherical PMMA powder resin | 5.0 |
| 13) Ion-exchanged water | Balance |
| 14) Glycerin | 4.0 |
| 15) Polyethylene glycol | 1.0 |
| 16) Antiseptic | suitable amount |
| 17) Stabilizer | suitable amount |
| 18) Perfume | suitable amount |

Preparation Method

All 1) to 9), 12), and all 16) to 18) were dissolved at 85° C., and then 10) and 11) we added and dispersed (oil phase). 14) and 15) were added in 13) and homogeneously dispersed (water soluble phase). The oil phase was added into the water soluble phase. The mixture was kept at 85° C. for 100 minutes with stirring. Then the mixture was gradually cooled to 45° C. with stirring.

EXAMPLE 10

W/O Type Emulsified Foundation

| (Recipe) | Weight % |
|---|---|
| 1) Silicone-treated synthesized mica | 15.0 |
| 2) Silicone-treated sericite | 7.0 |
| 3) Silicone-treated titanium oxide | 12.0 |
| 4) Silicone-treated red iron oxide | 1.2 |
| 5) Silicone-treated yellow iron oxide | 2.3 |
| 6) Silicone-treated black iron oxide | 0.6 |
| 7) Silicic anhydride-coated micro zinc oxide (10 weight % of silicic anhydride, 0.02 μm of average particle diameter of zinc oxide) | 12.0 |
| 8) Spherical PMMA powder | 4.0 |
| 9) Cyclomethycone | Balance |
| 10) Dimethyl polysiloxane | 4.0 |
| 11) Squalane | 3.0 |
| 12) Polyether-modified silicone | 2.0 |
| 13) Sorbitan sesquiisostearate | 1.0 |
| 14) Dispersing agent | suitable amount |
| 15) Dipropylene glycol | 2.0 |
| 16) Ion-exchanged water | 20.0 |
| 17) Paraben | suitable amount |
| 18) Anti oxidation agent | suitable amount |
| 19) Perfume | suitable amount |

Preparation Method

All 1) to 14) were mixed at 85° C. (oil phase). 15) was dissolved in 16) (water soluble phase). The oil phase was added into the water soluble phase with stirring at 85° C. for 100 minutes, and all 17) to 19) was added. Then the mixture was gradually cooled to 45° C. with stirring.

EXAMPLE 11

White Powder

| (Recipe) | Weight % |
|---|---|
| 1) Talc | Balance |
| 2) Synthetic mica | 22.0 |
| 3) Silicic anhydride-coated micro zinc oxide | 13.0 |
| (20 weight % of silicic anhydride, | |
| 0.03 μm of average particle diameter of zinc oxide) | |
| 4) Spherical silicone powder | 4.0 |
| 5) Squalane | 3.0 |
| 6) Paraben | suitable amount |
| 7) Perfume | suitable amount |

Preparation Method

All 1) to 6) were sufficiently mixed by a blender, and 7) was spread into the mixture with mixing by a blender.

EXAMPLE 12

O/W Type Emulsified Foundation

| (Recipe) | Weight % |
|---|---|
| 1) Sericite | 17.0 |
| 2) Mica | 20.0 |
| 3) Silicic anhydride-coated zinc oxide | 8.0 |
| (10 weight % of silicic anhydride, | |
| 0.03 μm of average particle diameter of zinc oxide) | |
| 4) Red iron oxide | 0.3 |
| 5) Yellow iron oxide | 1.2 |
| 6) Black iron oxide | 0.6 |
| 7) Spherical polyethylene powder | 6.0 |
| 8) Squalane | 10.0 |
| 9) Olive oil | 10.0 |
| 10) Stearic acid | 2.0 |
| 11) Glycelyl monostearate | 2.0 |
| 12) POE(40)sorbitan monostearate | 2.0 |
| 13) Glycerin | 5.0 |
| 14) Triethanolamine | 0.8 |
| 15) pH Adjusting agent | suitable amount |
| 16) Antiseptic | suitable amount |
| 17) Ion-exchanged water | Balance |

Preparation Method

All 1) to 12) were mixed to dissolve at 85° C. (oil phase). All 13) to 15) were dissolved in 17) (water soluble phase). The oil phase was added into the water soluble phase. The mixture was kept at 85° C. for 100 minutes with stirring. Then the mixture was gradually cooled to 45° C. with stirring.

EXAMPLE 13

O/W Type Emulsified Cosmetic Base

| (Recipe) | Weight % |
|---|---|
| 1) Ion-exchanged water | Balance |
| 2) Glycerin | 20.0 |
| 3) 1,2-Pentane diol | 3.0 |
| 4) 1,3-Butylene glycol | 1.0 |
| 5) Liquid paraffin | 7.5 |
| 6) Isostearic acid | 0.5 |
| 7) Ascorbic acid (a whitening agent) | 0.2 |
| 8) Matricaria essence (a whitening agent) | 0.1 |
| 9) Yukinosita essence (a whitening agent) | 0.3 |
| 10) Di-2-ethyl hexyl Phthalate | 0.3 |
| 11) Spherical silica | 4.0 |
| 12) Composite material | 5.0 |
| between silicic anhydride and zinc oxide | |
| (40 weight % of silicic anhydride, | |
| 0.03 μm of average particle diameter of zinc oxide) | |
| 13) Talc | 5.0 |
| 14) Stabilizer | suitable amount |
| 15) Perfume | suitable amount |

Preparation Method

All 5) to 14) were dissolved at 85° C. (oil phase). All 2) to 4) were dissolved in 1) (water soluble phase). The oil phase was added into the water soluble phase. The mixture was kept at 85° C. for 100 minutes with stirring. Then the mixture was gradually cooled to 45° C. with stirring.

EXAMPLE 14

Anhydrous Eye Shadow

| (Recipe) | Weight % |
|---|---|
| 1) Dimethicone | 10.0 |
| 2) Ester oil | 10.0 |
| 3) Liguid paraffin | Balance |
| 4) Squalane | 10.0 |
| 5) Sorbitan sesquiisostearate | 1.0 |
| 6) Polyethylene wax | 8.0 |
| 7) Ceresin wax | 3.0 |
| 8) Mica | 7.0 |
| 9) Spherical cellulose powder | 5.0 |
| (About 6 μm of its particle diameter) | |
| 10) Interference type mica-titanium particle | 8.0 |
| 11) Composite material | 7.0 |
| between silicic anhydride and zinc oxide | |
| (35 weight % of silicic anhydride, | |
| 0.01 μm of average particle diameter of zinc oxide) | |
| 12) Kaolin | 10.0 |
| 13) Anti-oxidative agent | suitable amount |
| 14) Perfume | suitable amount |

Preparation Method

All 1) to 7) were mixed to dissolve at 85° C. and all 8) to 12) were mixed thereto with stirring. Then 13) and 14) were added into the mixture with stirring. Then the mixture was filled up in a container and cooled.

EXAMPLE 15

Lipstick

| (Recipe) | Weight % |
|---|---|
| 1) Polyethylene wax | 10.0 |
| 2) Ceresin wax | 3.0 |
| 3) Lanolin | 20.0 |
| 4) Polybutene | 20.0 |
| 5) Octyl methoxycinnamate | 5.0 |
| 6) Dimethycone | 12.0 |

-continued

| | |
|---|---|
| 7) Ester oil | Balance |
| 8) Titanium oxide | 4.5 |
| 9) Red No. 201 | 0.5 |
| 10) Red No. 202 | 1.1 |
| 11) Red No. 223 | 0.3 |
| 12) Spherical polyethylene powder (About 5 μm of its particle diameter) | 3.0 |
| 13) Red-iron oxide coated interference type mica-titanium particle | 12.0 |
| 14) Silicic anhydride-coated zinc oxide (20 weight % of silicic anhydride, 0.03 μm of average particle diameter of zinc oxide) | 5.0 |
| 15) Boron nitride powder (average particle diameter 15 μm) | 5.0 |
| 16) Anti-oxidative agent | suitable amount |
| 17) Perfume | suitable amount |

Preparation Method

All 1) to 7) were dissolved with heating at 85° C. All 8) to 15) were added into the solution with stirring, and then 16) and 17) were added into the mixed solution with stirring. Then the mixture was filled up in a container and cooled.

EXAMPLE 16

Powder Foundation for Dual Purpose

| (Recipe) | Weight % |
|---|---|
| 1) Silicone-treated sericite | 13.0 |
| 2) Silicone-treated mica | Balance |
| 3) Silicone-treated talc | 15.0 |
| 4) Silicic anhydride-coated zinc oxide (20 weight % of silicic anhydride, 0.03 μm of average particle diameter of zinc oxide) | 5.0 |
| 5) Aluminium stearate-treated micro-particle titanium oxide | 6.0 |
| 6) Silicone-treated titanium oxide | 9.0 |
| 7) Silicone-treated red iron oxide | 1.2 |
| 8) Silicone-treated yellow iron oxide | 2.5 |
| 9) Silicone-treated black iron oxide | 0.9 |
| 10) Barium sulfate powder | 7.0 |
| 11) Polyurethane powder | 1.0 |
| 12) Elastic silicone powder | 5.0 |
| 13) Polyethylene powder | 2.0 |
| 14) Interference type mica-titanium particle | 4.0 |
| 15) Paraben | suitable amount |
| 16) Dimethyl polysiloxane | 3.0 |
| 17) Methylphenyl polysiloxane | 2.0 |
| 18) Vaseline | 2.0 |
| 19) Octyl methoxycinnamate | 3.0 |
| 20) Sorbitan sesquiisostearate | 1.0 |
| 21) Polyether silicone | 1.0 |
| 22) Anti-oxidative agent | suitable amount |
| 23) Perfume | suitable amount |

Preparation Method

All 1) to 22) were mixed at 85° C. and then 23) was homogeneously spread.

EXAMPLE 17

Powder Foundation for Dual Purpose

| Recipe | Weight % |
|---|---|
| 1) Organofluorinated silicone-treated sericite | 22.0 |
| 2) Organofluorinated silicone-treated mica | Balance |
| 3) Organofluorinated silicone-treated kaolin | 10.0 |
| 4) Silicic anhydride-coated zinc oxide (10 weight % of silicic anhydride, 0.3 μm of average particle diameter of zinc oxide) | 7.0 |
| 5) Silicone-treated micro particle titanium oxide | 8.0 |
| 6) Organofluorinated silicone-treated titanium oxide | 9.0 |
| 7) Organofluorinated silicone-treated red iron oxide | 1.2 |
| 8) Organo fluorinated silicone-treated yellow iron oxide | 2.5 |
| 9) Organo fluorinated silicone-treated black iron oxide | 0.9 |
| 10) Spherical silicone powder | 8.0 |
| 11) Lauroyl lysine-coated titanium oxide | 4.0 |
| 12) Paraben | suitable amount |
| 13) Dimethylpolysiloxane | 4.0 |
| 14) Polyethylene glycol | 2.0 |
| 15) Fluoro polyether | 2.0 |
| 16) Octyl methoxycinnamate | 2.0 |
| 17) Sorbitan sesquiisostearate | 1.0 |
| 18) Anti-oxidative agent | suitable amount |
| 19) Perfume | suitable amount |

Preparation Method

All 1) to 18) were mixed at 85° C. and then 19) was homogeneously spread.

EXAMPLE 18

Wiping off Preparation for Cleaning

| (Recipe) | Weight % |
|---|---|
| 1) Ion-exchanged water | 91.945 |
| 2) Salt (registerd in Japan pharmaceutical codex) | 0.35 |
| 3) Dipropylene glycol | 2.0 |
| 4) Sodium hexa-metaphosphate | 0.005 |
| 5) Silicic anhydride-coated zinc oxide powder | 5.0 |
| 6) Bentonite | 0.5 |
| 7) Methyl paraben | 0.1 |
| 8) Polyoxyethylene 2-Octyl dodecyl ether | 0.1 |

Preparation Method

All 2) to 8) were dissolved and sufficiently dispersed into 1) with heating at 85° C. Then the mixed solution was impregnated into a nonwoven fabric.

EXAMPLE 19

Paper Powder

| (Recipe) | Weight % |
|---|---|
| 1) Colorants | 25.0 |
| 2) Silicic anhydride-coated zinc oxide | 3.0 |
| 3) Carboxymethyl cellulose | 0.2 |
| 4) Sodium dehydroacetate | 0.1 |
| 5) Sodium metaphosphate | 0.2 |
| 6) Polyoxyethylene sorbitan monoleate (20 E.O.) | 0.2 |
| 7) Perfume | 0.1 |
| 8) Purified water | Balance |

Preparation Method

A coating solution prepared by mixing all 1) to 7) into 8) was coated on a paper. Then the coated paper was dried.

All of the external preparation for skin of examples 1 to 19 showed adsorption effect and activation inhibition effect on a plasminogen activator, and showed an excellent improvement and prevention effect for dermatitis caused by skin contact with a material, psoriasis, atopic dermatitis and rough skin or pimples which a healthy person usually experiences.

What is claimed is:

1. A method for improving morbid dermatitis of atopic dermatitis and pimpled skin, which comprises topically applying a composition comprising a zinc oxide powder coated with silica to a skin affected by said morbid dermatitis thereby providing a plasminogen activator inhibitor which inhibits a plasminogen activator on the skin.

2. The method according to claim 1, wherein said zinc oxide is coated with 0.1 to 70 percent by weight of silica based on a weight of the zinc oxide.

3. The method according to claim 2, wherein said zinc oxide has an average particle diameter of less than 0.2 $\mu$m.

4. A cosmetic method for simultaneously improving morbid dermatitis of atopic dermatitis and pimpled skin, which comprises applying a cosmetic composition comprising a zinc oxide powder coated with silica to skin which is affected by said morbid dermatitis thereby providing a plasminogen activator inhibitor.

5. The method according to claim 4, wherein said zinc oxide is coated with 0.1 to 70 percent by weight of silica based on a weight of the zinc oxide.

6. The method according to claim 5, wherein said zinc oxide has an average particle diameter of less than 0.2 $\mu$m.

7. A method for inhibiting an activity of a plasminogen activator in the skin affected by morbid dermatitis, which comprises applying a composition comprising a zinc oxide powder coated with silica to the skin and adsorption of plasminogen activator onto said powder.

8. A method for preventing rough skin, which comprises applying a composition comprising a zinc oxide powder coated with silica to the skin whereby the zinc oxide powder coated with silica adsorbs a plasminogen activator on the skin to inhibit the plasminogen activator.

9. The method according to claim 8, wherein said zinc oxide is coated with 0.1 to 70 percent by weight of silica based on a weight of the zinc oxide.

10. The method according to claim 9, wherein said zinc oxide has an average particle diameter of less than 0.2 $\mu$m.

11. The method according to claim 7, wherein said zinc oxide is coated with 0.1 to 70 percent by weight of silica based on a weight of the zinc oxide.

12. The method according to claim 7, wherein said zinc oxide has an average particle diameter of less than 0.2 $\mu$m.

* * * * *